(12) United States Patent
Chavanne

(10) Patent No.: US 6,643,018 B2
(45) Date of Patent: Nov. 4, 2003

(54) OPTICAL SCATTERING MONITOR

(75) Inventor: Sylvie Chavanne, Saint-Etienne (FR)

(73) Assignee: Millipore Corporation, Billerica, MA (US)

( * ) Notice: Subject to any disclaimer, the term of this patent is extended or adjusted under 35 U.S.C. 154(b) by 11 days.

(21) Appl. No.: 09/895,467

(22) Filed: Jun. 29, 2001

(65) Prior Publication Data
US 2002/0027656 A1 Mar. 7, 2002

(30) Foreign Application Priority Data
Aug. 2, 2000 (IE) ............................................. S20000617

(51) Int. Cl.[7] .............................................. G01N 21/00
(52) U.S. Cl. ....................................... 356/338; 356/337
(58) Field of Search ................................. 356/338, 300, 356/301, 302, 337, 336, 339, 341, 73, 72

(56) References Cited

U.S. PATENT DOCUMENTS

| 4,547,071 A |   | 10/1985 | Teitelbaum | 356/344 |
|---|---|---|---|---|
| 4,717,545 A |   | 1/1988 | Morris | 422/56 |
| 4,981,362 A |   | 1/1991 | deJong et al. | 356/436 |
| 5,325,170 A |   | 6/1994 | Bornhop | 356/128 |
| 5,359,904 A | * | 11/1994 | Luukkala | 356/73.1 |
| 5,426,501 A |   | 6/1995 | Hokanson et al. | 356/335 |
| 5,428,443 A | * | 6/1995 | Kitamura et al. | 356/336 |
| 5,528,366 A |   | 6/1996 | Shortt | 356/344 |
| 5,840,258 A | * | 11/1998 | Hyppanen | 122/40 |
| 6,117,399 A | * | 9/2000 | Jorgensen et al. | 422/139 |
| 6,137,572 A |   | 10/2000 | DeFreez et al. | 356/336 |
| 6,319,468 B1 | * | 11/2001 | Sheppard et al. | 210/109 |
| 6,411,383 B1 |   | 6/2002 | Wyatt | 356/338 |
| 6,426,794 B1 |   | 7/2002 | Trainoff | 356/246 |

OTHER PUBLICATIONS

"Proteins: Protein/Aggregate Detection", Wyatt Technology Corporation Product Brochure (1999).
"Synthetic Polymers: Polymer Characterization by MALS", Wyatt Technology Corporation Product Brochure (1999).
"What is Linear Video" http://www.lord–ing.com/eng/linearvideo.htm (Oct. 30, 2002).
P. J. Wyatt, "Light scattering and the absolute characterization of macromolecules", Analytica Chimica Acta, 272 (1993) 1–40.

* cited by examiner

Primary Examiner—Thong Nguyen
Assistant Examiner—Joshua Pritchett
(74) Attorney, Agent, or Firm—John Dana Hubbard

(57) ABSTRACT

The present invention relates to the monitoring of polymers during their processing by the determination of optical scattering properties. According to one aspect of the invention, there is provided a monitoring system for a vessel for polymer processing and the like, comprising a monitoring cell for measuring the optical properties of the contents of the vessel, a feed path and a return path both connecting the cell to the vessel, and a pump connected in the feed or return path. According to another aspect of the invention there is provided a monitoring cell for measuring the optical properties of the contents of the cell, including a source for generating a laser beam through the cell, and a detector for detecting light scattered from the laser beam, preferably a linear camera and an optical system for focusing scattered light thereon.

9 Claims, 1 Drawing Sheet

OPTICAL SCATTERING MONITOR

The present invention relates to the monitoring of chemical processes and materials, and more specifically to monitoring by the determination of optical scattering properties.

BACKGROUND OF THE INVENTION

A particular application of the present system is to monitor the condition of polymers during their processing. Such polymer processing yields polymer solutions which change as the processing proceeds. It is therefore necessary to monitor the polymer solution as processing proceeds, so that the progress of the processing can be followed and the processing stopped or modified at the appropriate time, or subsequent processing steps may be modified to account for the condition of the polymer solution.

An established monitoring technique for this is to use light scattering. In one known system, for example, a sample of the solution is placed in a cell through which a laser beam is passed, and three photodetectors are arranged to detect light scattered at three respective angles (approximately 45°, 90°, and 135° to the laser beam).

In the context of polymer processing, it is conventional to take samples from the reaction vessel containing the solution at suitable intervals. Each sample is placed in a cell and its optical properties measured. The plant operator can therefore follow the progress of the mix and control it accordingly.

We have realized that this technique has a number of disadvantages, both apparent and real.

One disadvantage is that the temperature of the sample is likely to change, from the temperature of the reaction vessel to room temperature, before its properties are measured. However, the properties of the sample will generally change consistently with temperature, and the temperature of the reaction vessel will normally be measured anyway, so it will sometimes be possible to make allowances for this problem.

Another disadvantage with off-line sampling is that the solution tends to lose solvent during removal and testing, which changes the solvent: polymer ratio and the properties of the product being tested.

Further problems are that an operator must be available to take the sample and that there will be a time delay between taking the sample and determining its properties. These problems will make the operator's task more difficult, since the taking of the samples will distract the operator and the time delay will result in the operator being given somewhat out-of-date information.

SUMMARY OF THE INVENTION

According to this aspect of the invention, there is provided a monitoring system for a reaction vessel for polymer processing and the like, comprising a monitoring cell for measuring the optical properties of the contents of the reaction vessel, a feed path and a return path both connecting the cell to the reaction vessel, and a pump connected in the feed or return path.

A significant advantage of this arrangement is that laser speckle in the monitoring cell is effectively eliminated, because the liquid being monitored is moving through the cell. No signal smoothing arrangements are therefore required.

This arrangement also makes the monitoring data available immediately, and ensures that the liquid being monitored is at substantially the same conditions (temperature and pressure and the solvent:polymer ratio) as in the reaction vessel. The fact that the temperature is maintained also means that liquids which would set or gel or otherwise be inconvenient to monitor at room temperature can be monitored without difficulty.

Turning to another aspect of optical liquid monitoring, the conventional arrangement is, as mentioned above, to pass a laser beam through the monitoring cell and provide one or more photodetectors arranged at suitable angles to the laser beam. One known system uses a single photodetector which detects backscattered light at an angle of 153°; dual angle systems are known; and another, as mentioned above, uses three photodetectors at angles of approximately 45°, 90°, and 135°.

The invention may be used to monitor polymers which are in solution, at least partially, or which are carried in liquid as a dispersion or emulsion, but not for melted polymers.

A wide variety of materials may be monitored, and the number and arrangement of photodetectors will normally be chosen in dependence on how far the particular materials to be monitored are likely to vary. If the materials to be monitored are tightly determined and their optical properties are well known, a single photodetector may be satisfactory; if the materials vary more widely, then two or three photodetectors may be used.

For a sample of relatively uniform material, the scattering light intensity curve (obtained by plotting the scattering light intensity against the angle of detection) is likely to have a fairly smooth curve shape. The position and height of the peak of the curve can of course both vary substantially, and the steepness of each of the sides of the curve can also vary. The selection of the positions of the photodetectors can therefore present difficulties, even with the use of three photodetectors. Further, there may be situations where there may be mixtures of different materials, in which case the curve may have a flattened peak or there may even be two or more curves. This can be overcome by providing more photodetectors, but that increases the cost and complexity of the monitoring cell.

The general object of this aspect of the invention is to alleviate the difficulties in selecting the number and positions of the photodetectors.

According to this aspect of the invention there is provided a monitoring cell for measuring the optical properties of the contents of the cell, including a source for generating a laser beam through the cell, and a detector for detecting light scattered from the laser beam, preferably a linear camera and an optical system for focusing scattered light thereon.

With this arrangement, the light scattered at any particular angle or set of angles can immediately be determined, by suitable sampling of the output scan of the camera. If desired, however, a complete graph of the scattered light against scattering angle can automatically be generated. If, for example, a modified or new polymer process is being developed, such displays can be generated for the entire range of polymer conditions occurring during the development of the process, and can then be analysed and compared and a suitable set of monitoring angles chosen which will give good discrimination between polymer conditions which need to be distinguished.

A polymer processing system including a monitoring system embodying these aspects of the invention will now be described, by way of example, with reference to the drawings, in which:

IN THE FIGURES

DETAILED DESCRIPTION OF THE INVENTION

Figure 1:
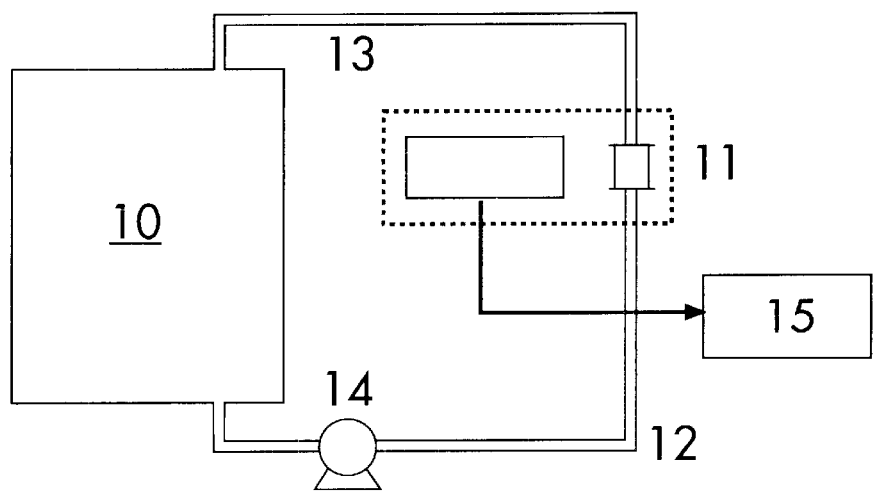
FIG. 1 is a general block diagram of the processing system.

FIG. 1 shows a reaction vessel 10 forming part of a polymer processing system. The vessel 10 has coupled to it a monitoring system comprising a monitoring cell 11, a feed path 12 connecting the vessel to the cell, a return path 13 connecting the cell back to the vessel, and a pump 14 connected in the feed path 12. The monitoring cell 11 is coupled to a processing unit 15, which processes the output of the monitoring unit to obtain and display a variety of useful parameters therefrom.

In operation, the pump 14 will normally be kept running continuously while the contents of the vessel 10 are being processed. The polymer solution can thus be monitored continuously. Further, the polymer solution is monitored at substantially the temperature of the bulk of the liquid in the reaction vessel, so it can be monitored as long as it flows at that temperature, even though it may set or gel at room temperature. The solution may be monitored without solvent loss which avoids changing the solvent:polymer ratio, which in turn affects the results obtained in the prior art.

One can add thermal insulation and/or heaters (such as electric cable heaters, water or steam jackets, etc.) to the feed and return lines to reduce heat loss.

Figure 2:
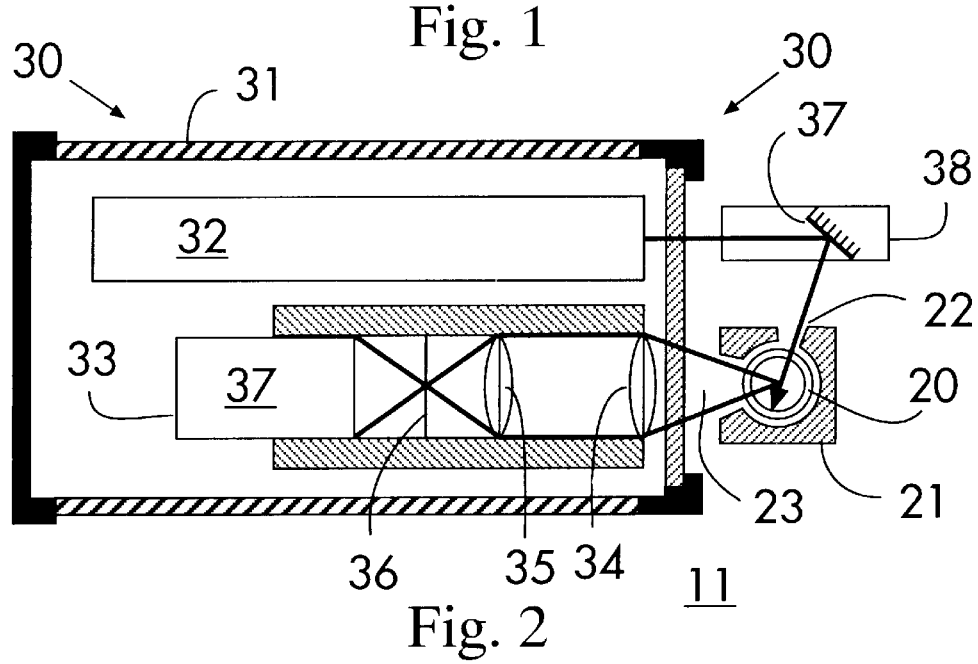
FIG. 2 is a general sectional diagram of the monitoring cell.

FIG. 2 is a more detailed diagram of the monitoring cell 11. A glass tube 20, shown in cross section, is connected between the feed and return paths 12 and 13, so that the liquid to be monitored flows through it. The tube 20 is surrounded by a steel jacket 21 to increase its strength; the jacket 21 has light path openings 22 and 23. As an alternative to a steel jacket, other metals such as nickel, copper or aluminium may be employed, or one may use a suitable plastic (which is preferably inert under the conditions and substances encountered) such as PTFE, or an epoxy with or without glass reinforcement. The jacket must be opaque to reduce secondary scattering from its walls or the outside. Preferably it is coated or painted black on the inner surface, which may also help absorb some of the misdirected light and reduce interference. Optionally, one can place a light absorber such as a pad of carbon directly opposite the point of entry of light into the cell to further reduce stray scattering.

The optical system 30 is largely confined within an explosion-proof box 31 with a glass window 40; the box 31 contains a laser 32 and a sensing system 33. The laser should be selected (in terms of power and wavelength) to match the liquid one is monitoring. This will vary depending on the polymer and the desired level of intensity, but typically, a laser from about 1 to 10 mW is appropriate, operating at a preferred wavelength of 695 to 850 nm.

The laser produces a light beam which is reflected by a mirror 39 through opening 22 to the glass tube 20; light is scattered through the opening 23 to the sensing system 33, which has an angular field of view of approximately 60°. The mirror 39 may be movably mounted on a mounting block 38, so that the angle between the laser beam from the mirror and the central optical axis of the sensing system can be adjusted.

The sensing system 33 comprises a first lens 34 which converges the scattered light into a parallel beam, a second lens 35 which converges the beam to a focus, pin-hole diaphragm 36 placed at the focal plane to allow only light from the centre of the tube 20 through, and a linear camera 37. The camera 37 may be of any convenient type, such as a traditional scanning beam type of a CCD type, with a single scanning direction (rather than the 2-dimensional scanning type used for normal video pictures). A suitable camera is available from Lord Ingenierie, of Nozay, France, under the reference CNL2048/Sh, which may be used with an acquisition card No. ASL 8220.

In addition to the light scattering system described, additional monitors can be added inline, such as temperature gauges, pressure sensors, viscometers, etc.

Figure 3:
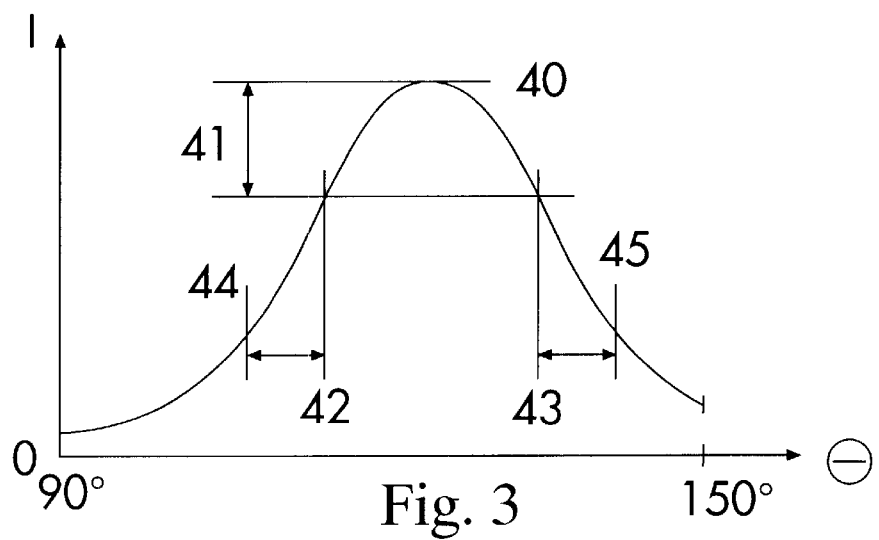
FIG. 3 is an illustrative scattering angle graph.

FIG. 3 shows a typical scattering curve. The horizontal axis shows the angle θ between the laser beam emerging from the tube 20 and the scattered light, and the vertical axis shows the intensity I of the light scattered at that angle. The scanning of the TV camera corresponds to the horizontal axis, and the amplitude of its output corresponds to the vertical axis. The output can of course be converted to digital form if desired.

The scattering curve shown is a typical curve obtained from a fairly simple liquid. As shown, the curve consists of a single peak. Depending on the details of the process being carried out in the reaction vessel 10, the amplitude of the curve, the position of the peak, and the slopes of each of the two sides of the curve may vary.

If the behaviour of the reaction is well enough understood, it may be possible to select a few specific angles, or even only one angle, by which the progress of the reaction can be adequately monitored. However, in order to determine the appropriate angles, the whole curve needs to be examined for a range of liquid conditions, to determine for example the position of the peak and the angular distances from each side of the peak where the intensity measurements will give the best indications of the slopes of the sides of the curve.

If the amplitude of the curve, the position of the peak, and the slopes of each of the two sides of the curve are all variable, then no set of fixed angular positions is likely to give a satisfactory indication of the state of the liquid. For this, the entire curve needs to be available for processing, although the processing itself may be relatively simple. For example, the height 42 of the peak can be determined, and reduced by a suitable fraction 43. This will enable two points 44 and 45 on the sides of the curve to be determined. From these, a point representing the (angular) position of the peak of the curve can be calculated. Also, by taking angles 46 and 47 fixed distances on each side of the angles 44 and 45 and determining the amplitudes at those angles, the slopes of the two sides of the curve can readily be determined. Thus a variety of potentially important parameters, such as the position and height of the curve peak and the slopes of the two sides, can readily be derived with only slight calculation. The resulting parameters can be displayed by the processing unit 15.

The processing unit 15 can also include a graphic display device which displays the scattering curve, possibly together with indications of the values being used to determine the parameters being calculated. This will also allow the operator to check that the liquid being monitored is in fact behaving broadly in the expected way, i.e. that the scattering curve is of broadly the expected shape. It will also allow the behaviour of relatively unknown or poorly understood liquids to be monitored in detail.

What is claimed:

1. A monitoring system, useful for illuminating and acquiring scattered light intensity data from a flowing polymer solution, the monitoring system comprising:

a vessel for processing said polymer solution;

a monitoring cell comprising a laser, a photodetector, and a flow tube, wherein said laser is capable of producing a beam of light that is scattered by said polymer solution, wherein said flow tube is capable of allowing said polymer solution to flow therethrough, and wherein said photodetector is a CCD having a single scanning direction positioned to receive light passed through and scattered by said polymer solution in said flow tube and is capable of measuring the intensity of said scattered light;

a feed path and a return at both connecting the monitoring cell to the vessel, said flow tube being connected between said feed path and said return path; and a pump connected in th feed or return path and capable of effecting flow of said polymer solution from said vessel to said monitoring cell, said pump configured to run continuously during said light intensity measurement.

2. The monitoring system of claim 1, further comprising thermal insulation applied to the feed and return paths.

3. The monitoring system of claim 2, further comprising a heater coupled to the feed and return paths.

4. The monitoring system of claim 1, further comprising an adjustably mounted mirror, and wherein:
   (a) said flow tube further comprises an opaque jacket, said opaque jacket having a first and second light path opening;
   (b) said laser and said photodetector are contained in a single box;
   (c) said laser, said mirror, and said flow tube are arranged so that light produced by said laser is reflected by said mirror toward said first opening into said flow tube; and
   (d) said second opening and said photodetector are arranged so that, in the presence of said polymer solution, light directed into said flow tube is scattered toward said photodetector through said second opening.

5. The monitoring system of claim 4, wherein said flow tube further comprises light absorbing material on an inner surface of said flow tube.

6. The monitoring system of claim 1, wherein said laser is capable of operating at a wavelength of from approximately 695 nm to approximately 850 nm, and at approximately 1 to 10 mW.

7. The monitoring system of claim 1, further comprising a processing unit, the processing unit capable of (a) obtaining from said photodetector said light intensity measurement, (b) processing said measurement sufficiently to generate at least a portion of a scatter graph, and (c) determining either a peak of said scatter graph and/or the slopes of the curve on either side of said peak.

8. A monitoring system, useful for illuminating and acquiring scattered light intensity data from a flowing polymer solution, the monitoring system comprising:

a vessel for processing said polymer solution;

a monitoring cell comprising a laser, a photodetector, and a flow tube, wherein said laser is capable of producing a beam of hg t that is scattered by said polymer solution, wherein said flow tube is capable of allowing said polymer solution to flow therethrough, and wherein said photodetector is positioned to receive light passed through and scattered by said polymer solution in said flow tube and is capable of measuring the intensity of said scattered light;

a feed path and a return path both connecting the monitoring cell to the vessel, said flow tube being connected between said feed path and said return path; and a pump connected in the feed or return path and capable of effecting flow of said polymer solution from said vessel to said monitoring cell, said pump configured to run continuously during said light intensity measurement;

wherein said vessel, said feed path, said pump, and said monitoring cell are configured such that the solvent-:polymer ratio of said polymer solution remains substantially the same as said polymer solution flows from said vessel to said monitoring cell.

9. A method for the non-destructive monitoring of a solvated polymer composition being processed, comprising, transporting at least a portion of said composition from a vessel in which said composition is being processed through a flow path connected to said vessel, which has a monitoring cell incorporated into said flow path, said cell suitable to allow passage of a coherent beam of energy through said cell, said transport of the composition through the cell being done at a rate that reduces laser speckle of the scattered beam to an amount that is essentially undetectable; and detecting the scattered energy of at least a portion of said beam, generating a sensing signal from said detected portion, and analyzing said signal by signal processing means to characterize the properties of said composition.

* * * * *